(12) United States Patent
Lee

(10) Patent No.: US 6,305,777 B1
(45) Date of Patent: Oct. 23, 2001

(54) APPARATUS AND METHOD FOR MEASUREMENT OF A LIQUID DROPLET

(75) Inventor: Tzong-Shyng Lee, Plainsboro, NJ (US)

(73) Assignee: Sarnoff Corporation, Princeton, NJ (US)

( * ) Notice: Subject to any disclaimer, the term of this patent is extended or adjusted under 35 U.S.C. 154(b) by 0 days.

(21) Appl. No.: 09/215,018

(22) Filed: Dec. 17, 1998

Related U.S. Application Data
(60) Provisional application No. 60/095,333, filed on Aug. 4, 1998.

(51) Int. Cl.⁷ .................................................. B41J 29/393
(52) U.S. Cl. ............................................................. 347/19
(58) Field of Search .................................. 347/19, 14, 23, 347/75, 81; 250/573; 356/379, 301; 372/101, 108

(56) References Cited

U.S. PATENT DOCUMENTS

| | | | |
|---|---|---|---|
| 4,429,995 | * | 2/1984 | Goulas .................................. 356/343 |
| 4,751,517 | * | 6/1988 | Crean et al. ............................ 347/75 |
| 5,430,306 | * | 7/1995 | Ix .......................................... 250/573 |
| 5,637,881 | * | 6/1997 | Burghard et al. ...................... 250/573 |

* cited by examiner

Primary Examiner—John Barlow
Assistant Examiner—Charles W. Stewart, Jr.
(74) Attorney, Agent, or Firm—William J. Burke

(57) ABSTRACT

An apparatus for measuring the characteristics of a droplet of a liquid, such as a droplet of ink, includes a laser for generating and projecting a beam of light along a path. The beam is directed into a photodetector, such as a photodiode, which detects the amount of light provided by the beam and provides an electrical signal corresponding to the amount of light detected. Adjacent the output end of the laser are lenses which focus the beam of light at a focal point and form the beam into a sheet at the focal point. An ink jet head is adjacent the path of the beam at the focal point. The ink jet head projects a droplet of ink to and through the sheet portion of the beam so as to change the amount of light detected by the photodetector. From the electrical signal output of the photodetector various characteristics of the droplet can be determined, such as the size, shaped and velocity of the droplet.

15 Claims, 2 Drawing Sheets

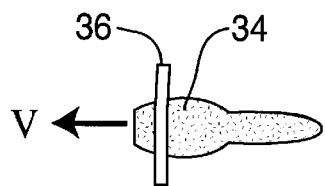
FIG. 3
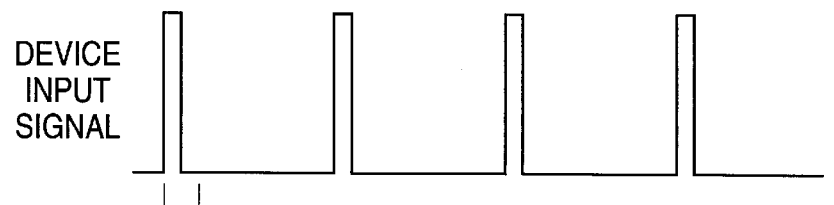
FIG. 4a DEVICE INPUT SIGNAL
FIG. 4b DETECTOR OUTPUT SIGNAL
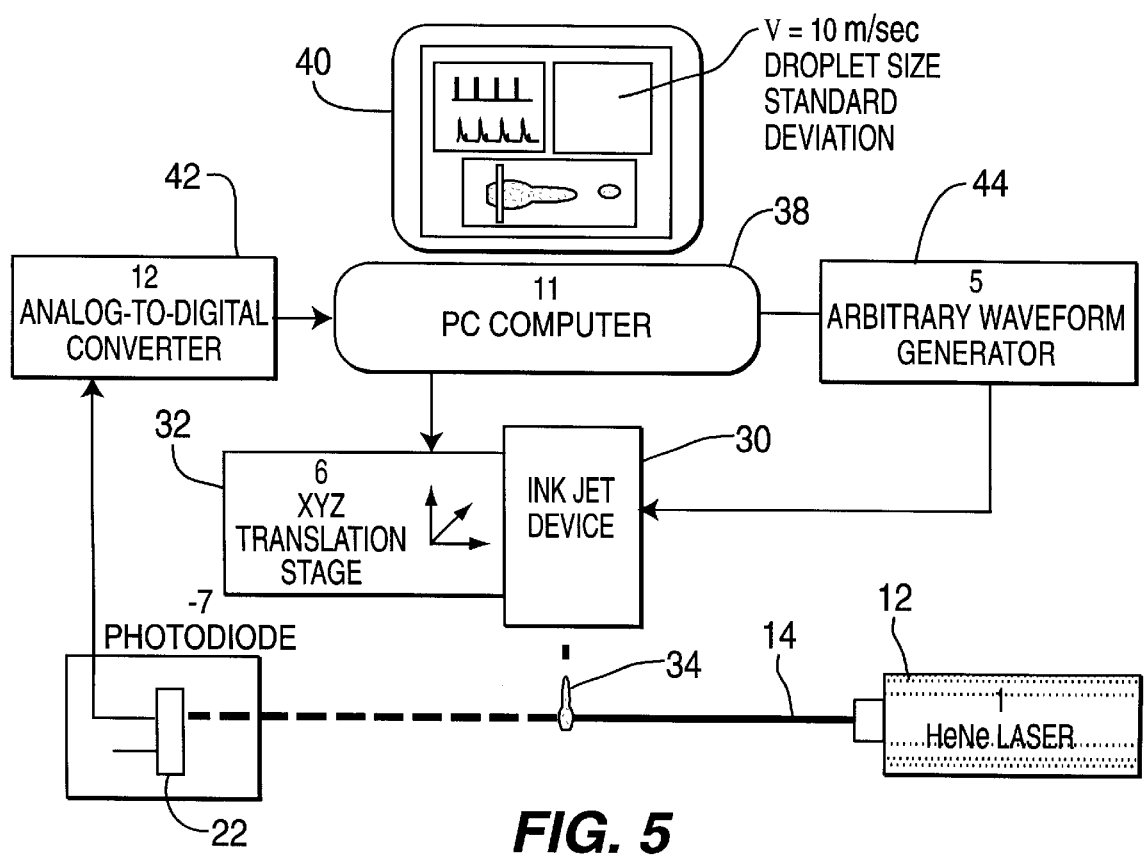
FIG. 5

APPARATUS AND METHOD FOR MEASUREMENT OF A LIQUID DROPLET

This application claims the benefit of U.S. Provisional Application Serial No. 60/095,333 filed Aug. 4, 1998.

FIELD OF THE INVENTION

The present invention relates to an apparatus and method for the measurement of a liquid droplet, and, more particularly to an apparatus and method for providing quantitative information about liquid droplets ejected by ink jet printer heads.

BACKGROUND OF THE INVENTION

In an ink jet printer, ink is supplied to a printer head which has a plurality of nozzles for ejecting droplets of ink onto a sheet of paper or the like to print words, pictures, etc. The characteristics of the ink droplets, such as the size, shape, velocity and frequency and stability of the droplet formation effect the characteristics of the lines, etc. which are printed. Therefore it would be desirable to be able to measure the various characteristics of ink droplets as ejected from a printer head to be able to determine how to control the printer head to achieve a print of desired characteristics.

SUMMARY OF THE INVENTION

A liquid droplet measuring apparatus includes means for generating and projecting a beam of illumination, and means for forming a portion of the beam into the shape of a sheet. Means is provided for forming and projecting a liquid droplet through the sheet portion of the beam of illumination. Means is also provided for detecting the beam after the droplet passes therethrough.

The method of the present invention for measuring a liquid droplet includes forming and projecting a beam of illumination along a path. A portion of the beam is formed into the shape of a sheet. A liquid droplet is projected through the sheet portion of the beam of illumination. The beam after the droplet passes therethrough is measured to determine a characteristic of the droplet.

BRIEF DESCRIPTION OF THE DRAWINGS

FIG. 3 is a schematic view showing a liquid drop passing through the light beam of the apparatus of the present invention;

FIGS. 4a and 4b are diagrams showing the device input signal and variations in the output signal from the apparatus of the present invention resulting from a liquid drop passing through the light beam; and FIG. 5 is a block diagram of the control system for the apparatus of the present invention.

DETAILED DESCRIPTION OF THE PRESENT INVENTION

Figure 1:
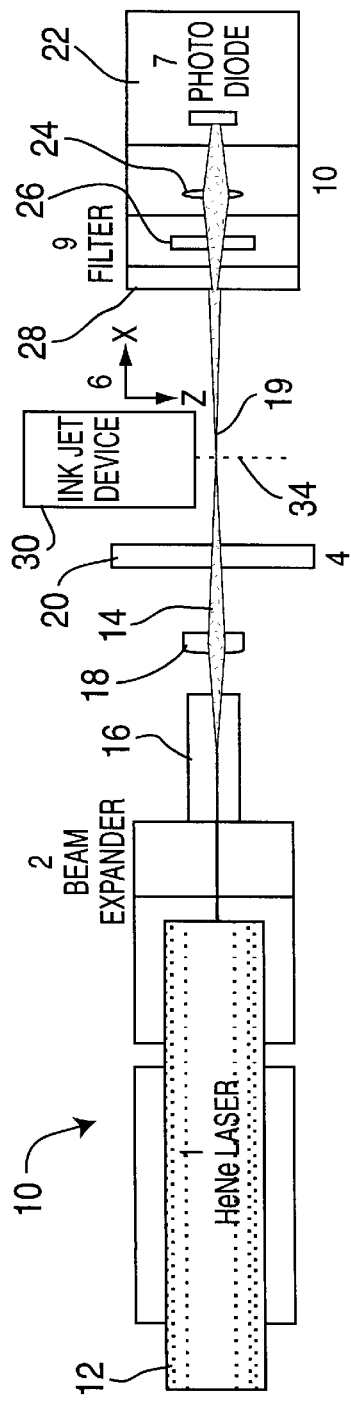
FIG. 1 is a top view of the apparatus of the present invention.
Figure 2:
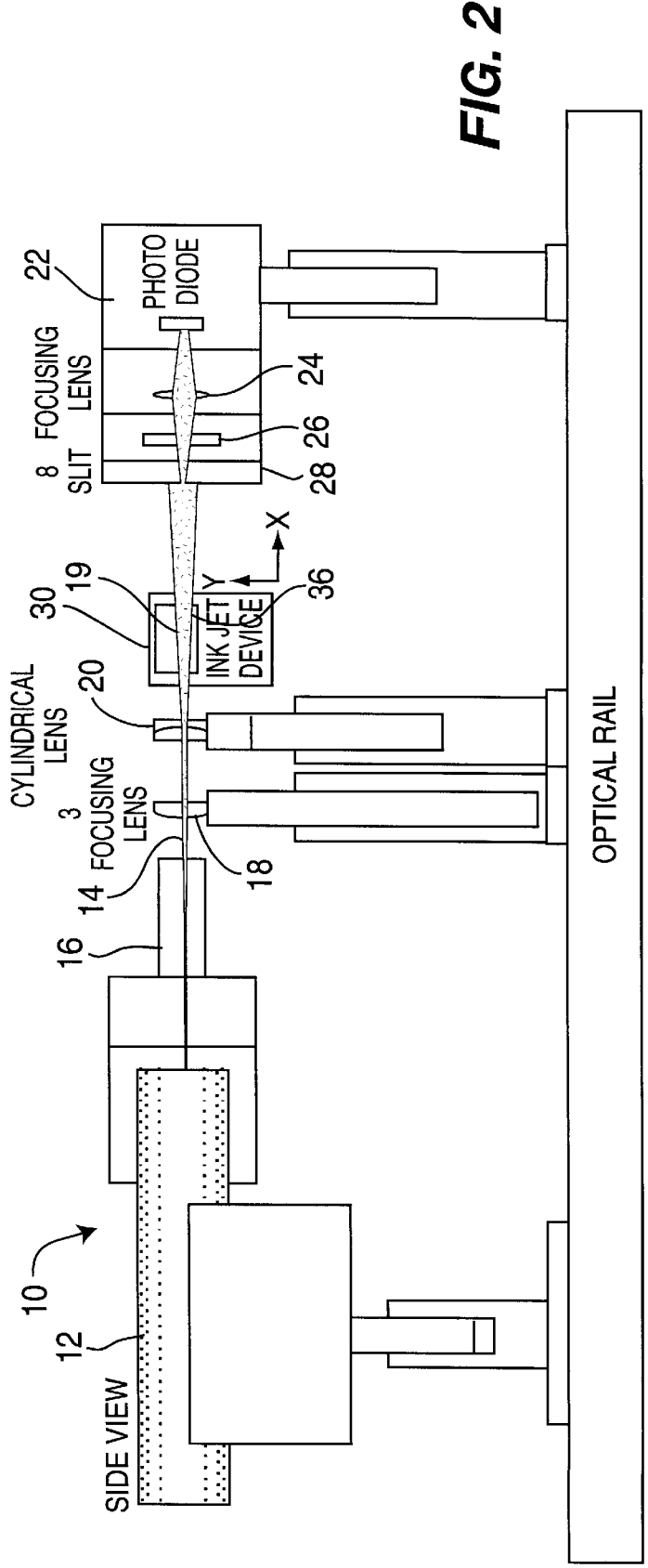
FIG. 2 is a side view of the apparatus shown in FIG. 3.

Referring initially to FIGS. 1 and 2, the liquid drop measuring apparatus of the present invention is generally designated as 10. Measuring apparatus 10 comprises a source 12 of a beam of illumination. Preferably, the source 12 is a laser, particularly a HeNe laser. The laser 12 can generate and emit a beam of light 14 along a relatively straight path. At the exit end of the laser 12 is a beam expander 16 which expands the size of the light beam 14. Next along the path of the light beam 14 is a focusing lens 18 for focusing the light beam 14 at a desired point 19 along the path of the light beam 14. Then there is a cylindrical lens 20 which forms the light beam 14 into the form of a micro sheet 36 at the focal point 19. The micro sheet 36 is preferably approximately 10 microns in thickness and 100 microns in height.

Along the beam path and spaced from the focus point 19 where the beam is in the form of a sheet is a photodetector 22 for receiving and detecting the beam of light 14. The photodetector 22 is preferably a PIN photodiode. In front of the photodetector 22 is a focusing lens 24. In front of the focusing lens 24 is an optical bandpass filter 26. In front of the filter 26 is a slit 28. The slit 28, filter 26 and focusing lens 24 serve respectively to aperture the beam size, discriminate the background lighting and collect the optical signal into the active area of the photodiode photodetector 22.

At the focus point 19 is in ink jet head 30 which has a plurality of nozzles, not shown, for emitting drops of liquid ink. The ink jet head 30 is positioned so that the emitting nozzles face the side of the sheet of the light beam. Thus, emitting drops of the liquid ink will be projected through the sheet of the light beam 14. The ink jet head 30 may be mounted on a translation stage 32 to permit the adjustment of the position of the ink jet head 30 so that the drops of the liquid ink will be properly projected through the sheet of the light beam 14.

In the operation of the measuring apparatus 10, the laser 12 is turned on to generate illumination, such as light, and emit the light as the beam 14 along the path to the photodetector 22. The size of the beam of light is first expanded by the beam expander 16 and then is focused as a micro light sheet at the focal point 19 by the focusing lens 18 and the cylindrical lens 20. The light beam 14 then passes through the slit 28, filter 26 and focusing lens 24 to the photodiode of the photodetector 22. The PIN photodiode is set to a reversed voltage mode in order for shadows to give positive signals. Referring to FIG. 4a, there is shown the output of the photodiode 22 from the normal input signal of the beam of light 14.

The ink jet head 30 is turned on to form and eject droplets of ink from a nozzle. The ink jet head 30 projects the ink droplet 34 through the micro sheet 36 of the light beam 14 at the focal point 19 as shown in FIG. 3. As the ink droplet 34 passes through the sheet 36 of the light beam 14, it will block out a portion of the light beam and thus create shadows that are detected by the photodiode 22. Variations in the size of the ink droplet 34 will vary the amount of the shadow and thus vary the electrical output of the photodiode 22. FIG. 4b shows the output of the photodiode 22 as a result of an ink droplet of the shape such as shown in FIG. 3 passing through the sheet 36 of the light beam 14. The shape of the signal provides an indication of the shape and size of the ink droplet 34. By moving the ink jet head 30 away from the sheet 36 of the light beam 14 a known distance and measuring the shift in the time delay between the device input signal and the detected signal (dT), the velocity of the ink droplet 34 can be estimated. The droplet velocity V at a location $(dS_2+dS_1)/2$, where $S_1$ and $S_1$ are the distances of the ink jet head 30 from the sheet 36 of the light beam 14, can be estimated by using $V=(dS_2-dS_1)/(dT_2-dT_1)$. The apparatus 10 can provide statistical information about the frequency and stability of the droplet formation. Performance characteristics can be calculated using phase averaging techniques and standard deviations of the droplet sizes and ejection rates.

Referring to FIG. 5 there is shown a control system for the apparatus 10 of the present invention. The control system includes a computer 38 having a visual display 40. The output of the photodiode 22 is connected to the computer 38 through an analog-to-digital converter 42. The computer 38 is connected to the translation stage 32 of the ink jet head 30 so as to permit the computer to control the movement of the ink jet head 30. The computer 38 is also connected to the ink jet head 30 through an waveform generator 44 so as to permit the computer to control the driving signals to the ink jet head 30. Thus, the computer 38 receives the output signals from the photodiode 22 and can display the signals on the display 40. The computer can also be programmed to convert the signals from the photodiode 22 to other information regarding the ink droplet 34 and provide such information on the display 40.

Thus, there is provided by the present invention and apparatus and method for measuring the characteristics of a droplet of ink. Such characteristics include the shape, size, velocity, frequency and stability of the ink droplet. This is all achieved by passing the ink droplet through a sheet form of a light beam and detecting the variation in the shadow provided by the droplet. Although the present invention has been described with regard to a droplet of ink, it can be used to measuring the characteristics of a droplet of any liquid.

What is claimed is:

1. A droplet measuring apparatus comprising:

a laser for generating and projecting a beam of light along a path;

a lens along the path of the beam forming a portion of said beam to the shape of a thin sheet at a focal point beyond the lens;

means for projecting a liquid droplet through the sheet portion of the beam: and means for detecting the beam after the droplet passes through the beam.

2. The apparatus of claim 4 further comprising a beam expander along the path of the beam between the laser and the focusing lens.

3. The apparatus of claim 1 wherein the means for detecting the beam of light comprises a photodetector.

4. The apparatus of claim 3 in which the photodetector comprises a photodiode having an active area.

5. The apparatus of claim 4 including means along the path of the beam and in front of the beam photodiode to aperture the size of the, discriminate any background lighting and focus the beam on the active area of the photodiode.

6. The apparatus of claim 1 in which the means for projecting the droplet into the sheet portion of the beam comprises a print head.

7. An apparatus for measuring the characteristics of a droplet of ink comprising:

a laser for generating and projecting a beam of light along a path;

a photodetector along the path of the beam for receiving the beam and providing an electrical output corresponding to the amount of the beam received;

lenses along the beam path between the laser and the photodetector for forming the beam in the form of a thin sheet at a focal point along the path beyond the lenses; and an ink jet head adjacent the beam path at the focal point for projecting droplets of ink toward and through the thin sheet of the beam.

8. The apparatus of claim 7 in which the lenses include a beam expander adjacent the laser, a focusing lens and a cylindrical lens.

9. The apparatus of claim 7 further comprising a computer having a visual display, and the output of the photodetector is connected to the computer to show the output on the display.

10. The apparatus of claim 9 in which the output of the photodetector is connected to the computer through an analog-to-digital converter.

11. The apparatus of claim 9 in which the computer is connected to the ink jet head to control driving signals to the head.

12. The apparatus of claim 11 in which the ink jet head is mounted on a translator stage for moving the head with respect to the beam path, and the computer is connected to the translator stage for controlling the movement of the ink jet head.

13. A method of measuring the characteristics of a droplet of a liquid comprising the steps of:

projecting a beam of light along a path;

focusing the beam at a focal point using a len;

forming the portion of the beam at the focal point into the shape of a sheet beyond the len;

detecting the beam after the beam passes the focal point and providing an electrical signal corresponding to the amount of light detected; and passing a liquid droplet through the sheet portion of the beam to varying the amount of light detected by the detecting step.

14. The method of claim 13 in which the beam of light is generated and projected along the path by a laser.

15. The method of claim 13 in which the beam is detected by a photodetector which provides an electrical output corresponding to the amount of light detected.

* * * * *

UNITED STATES PATENT AND TRADEMARK OFFICE
CERTIFICATE OF CORRECTION

PATENT NO.    : 6,305,777 B1
DATED         : October 23, 2001
INVENTOR(S)   : Leu It is certified that error appears in the above-identified patent and that said Letters Patent is hereby corrected as shown below:

<u>Title page,</u>
Item [54], replace " Lee" with -- Leu --.
Item [75], replace " Lee" with -- Leu --.

<u>Column 2,</u>
Line 60, please replace " $S_1$" with -- $S_2$ --.

<u>Column 3,</u>
Line 27, please replace claim 1 with the following:
-- 1. A droplet measuring apparatus comprising:
    a laser for generating and projecting a beam of light along a path;
    a focusing lens for focusing the beam at a focal point;
    a cylindrical lens along the path of the beam forming a portion of said beam to the shape of a thin sheet at the focal point;
    means for projecting a liquid droplet through the sheet portion of the beam; and
    means for detecting the beam as the droplet passes through the beam. --

Signed and Sealed this

Twenty-fifth Day of June, 2002

*Attest:*

*Attesting Officer*

JAMES E. ROGAN
*Director of the United States Patent and Trademark Office*